United States Patent
Cagle et al.

(10) Patent No.: US 10,667,878 B2
(45) Date of Patent: *Jun. 2, 2020

(54) SURGICAL SYSTEM WITH VOICE CONTROL

(71) Applicant: Ethicon LLC, Guaynabo, PR (US)

(72) Inventors: David J. Cagle, Cincinnati, OH (US); Eric Smith, Cincinnati, OH (US); Jeffrey L. Aldridge, Lebanon, OH (US); Mary E. Mootoo, Cincinnati, OH (US); Ryan Asher, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/013,343

(22) Filed: Jun. 20, 2018

(65) Prior Publication Data
US 2018/0311004 A1    Nov. 1, 2018

Related U.S. Application Data

(63) Continuation of application No. 15/383,564, filed on Dec. 19, 2016, now Pat. No. 10,028,794.

(51) Int. Cl.
*G10L 21/00* (2013.01)
*A61B 34/35* (2016.01)
(Continued)

(52) U.S. Cl.
CPC .............. *A61B 34/35* (2016.02); *A61B 34/25* (2016.02); *A61B 34/30* (2016.02); *A61B 34/74* (2016.02);
(Continued)

(58) Field of Classification Search
CPC ........ A61B 2017/002003; A61B 17/00; A61B 1/00041; A61B 34/70; A61B 1/005;
(Continued)

(56) References Cited

U.S. PATENT DOCUMENTS 6,468,265 B1    10/2002   Evans et al.
7,127,401 B2 *  10/2006   Miller .................... A61B 8/467
                                                   704/275
(Continued)

FOREIGN PATENT DOCUMENTS

KR      20120098342 A    9/2012
WO       WO-51486 A1     9/2000
(Continued)

OTHER PUBLICATIONS

U.S. Appl. No. 15/383,564, now U.S. Pat. No. 10,028,794, filed Dec. 19, 2016, David J. Cagle et al.
(Continued)

*Primary Examiner* — Vijay B Chawan
(74) *Attorney, Agent, or Firm* — Mintz Levin Cohn Ferris Glovsky and Popeo, P.C.

(57) ABSTRACT

A surgical system includes a plurality of voice sensors located in a surgical environment and configured to detect sound and generate a first plurality of signals. The surgical system also includes a position indicator, in proximity to a designated user, configured to indicate a first position of the designated user and generate a second signal representative of the first position. The surgical system further includes a processor configured to receive the first plurality of signals and the second signal and determine, based on the first plurality of signals, a second position. The processor is also configured to compare the detected sound with registered voice command of the designated user stored in a memory to verify the designated user's credentials, and send a command signal to a surgical instrument to carry out an operation related to the voice command based on at least one of the verification of the designated user's credentials, the first position and the second position.

19 Claims, 5 Drawing Sheets

(51) Int. Cl.
*A61B 34/00* (2016.01)
*A61B 34/30* (2016.01)
*A61B 17/00* (2006.01)
*A61B 90/50* (2016.01)
*A61B 90/00* (2016.01)
*A61B 34/20* (2016.01)
*G10L 17/00* (2013.01)
*G10L 15/22* (2006.01)

(52) U.S. Cl.
CPC ............ *A61B 2017/00203* (2013.01); *A61B 2017/00216* (2013.01); *A61B 2017/00221* (2013.01); *A61B 2034/2063* (2016.02); *A61B 2034/301* (2016.02); *A61B 2034/302* (2016.02); *A61B 2090/3612* (2016.02); *A61B 2090/502* (2016.02); *G10L 17/005* (2013.01); *G10L 2015/223* (2013.01)

(58) Field of Classification Search
CPC ... A61B 34/25; A61B 1/00149; A61B 1/0016; A61B 2017/00017; A61B 2017/00199; A61B 2017/00207; A61B 2017/00973; A61B 2090/372; A61B 34/10; A61B 34/30; A61B 34/37; A61B 34/74; A61B 5/00; A61B 5/064; A61B 5/7405; A61B 5/749; A61B 8/13; A61B 8/461; A61B 8/467; A61B 90/20; A61B 90/36; G10L 15/26; G10L 15/22; G10L 2015/223; G10L 15/00; G10L 15/08; G10L 15/142; G10L 15/20; G10L 15/32; G10L 17/00; G10L 17/22; G10L 2021/02166; G05B 15/02; G05B 19/042; G05B 2219/23386; G05B 2219/39389; G05B 2219/40168; G05B 2219/40195; G05B 2219/45123; H04R 1/028; H04R 1/08; H04R 3/005
USPC ..... 704/270, 275, 270.1, 231, 246; 606/130; 340/384.7, 3.54; 700/94, 275
See application file for complete search history.

(56) References Cited

U.S. PATENT DOCUMENTS

| | | | | |
|---|---|---|---|---|
| 7,259,652 B2* | 8/2007 | Wang | ................ | A61B 17/00 340/3.7 |
| 7,395,249 B2* | 7/2008 | Wang | ................ | G16H 40/63 706/14 |
| 7,921,017 B2* | 4/2011 | Claus | ................ | A61B 17/00 704/231 |
| 8,114,345 B2 | 2/2012 | Dlugos, Jr. et al. | | |
| 9,264,801 B2* | 2/2016 | Contolini | ................ | G06F 19/34 |
| 9,549,717 B2* | 1/2017 | Contolini | ................ | A61B 17/00 |
| 10,009,676 B2* | 6/2018 | Contolini | ................ | H04R 1/08 |
| 10,028,794 B2* | 7/2018 | Cagle | ................ | A61B 34/35 |
| 10,169,535 B2* | 1/2019 | Mentis | ................ | G06F 19/321 |
| 2002/0128846 A1 | 9/2002 | Miller | | |
| 2002/0183894 A1 | 12/2002 | Wang et al. | | |
| 2004/0034534 A1 | 2/2004 | Sander et al. | | |
| 2004/0124964 A1 | 7/2004 | Wang et al. | | |
| 2005/0033580 A1 | 2/2005 | Wang et al. | | |
| 2006/0142740 A1 | 6/2006 | Sherman et al. | | |
| 2006/0178559 A1 | 8/2006 | Kumar et al. | | |
| 2008/0021711 A1 | 1/2008 | Claus et al. | | |
| 2010/0100080 A1 | 4/2010 | Huculak et al. | | |
| 2011/0063429 A1* | 3/2011 | Contolini | ................ | A61B 17/00 348/77 |
| 2011/0276058 A1* | 11/2011 | Choi | ................ | B25J 9/1671 606/130 |
| 2012/0022696 A1 | 1/2012 | Aoussat et al. | | |
| 2013/0331859 A1 | 12/2013 | Kumar et al. | | |
| 2014/0153747 A1* | 6/2014 | Contolini | ................ | G06F 19/34 381/122 |
| 2015/0279368 A1* | 10/2015 | Contolini | ................ | G10L 15/08 704/246 |
| 2016/0125882 A1 | 5/2016 | Contolini et al. | | |
| 2016/0210411 A1 | 7/2016 | Mentis | | |

FOREIGN PATENT DOCUMENTS

| | | |
|---|---|---|
| WO | WO-2014151621 A1 | 9/2014 |
| WO | WO-2015143067 A1 | 9/2015 |

OTHER PUBLICATIONS

International Search Report and Written Opinion for International App. No. PCT/US2017/064599 dated Apr. 23, 2018 (11 pages).

\* cited by examiner

SURGICAL SYSTEM WITH VOICE CONTROL

CROSS-REFERENCE TO RELATED APPLICATIONS

This application is a continuation of U.S. patent. Ser. No. 15/383,564 entitled "Surgical System With Voice Control" filed on Dec. 19, 2016, which is hereby incorporated herein by reference.

FIELD

Methods and devices are provided for minimally invasive surgery, and in particular for providing voice control of a surgical instrument.

BACKGROUND

Minimally invasive surgical (MIS) instruments are often preferred over traditional open surgical instruments due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical environment with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical environment on a visual display at a location remote from the patient. The surgeon can typically perform the surgical procedure at the location remote from the patient whilst viewing the end effector movement on the visual display during the surgical procedure. While viewing typically a three-dimensional image of the surgical environment on the visual display, the surgeon performs the surgical procedures on the patient by manipulating master control devices at the remote location, which master control devices control motion of the remotely controlled instruments.

While significant advances have been made in the field of minimally invasive surgery, there remains a need for improved methods, systems, and devices for providing seamless control of surgical instrument based on voice commands.

SUMMARY

Methods, devices, and systems are provided for the use of voice commands to control one or more surgical instruments. In addition to issuing a command signal to a surgical instrument, a processor associated with the system also authenticates voice commands to ensure that the voice commands are actionable commands. A command is actionable when it has been authenticated by at least one authentication technique. In one embodiment, more than one authentication technique is required before a voice command is regarded as actionable.

A surgical system includes a plurality of voice sensors located in a surgical environment and configured to detect sound and generate a first plurality of signals. The surgical system also includes a position indicator, in proximity to a designated user, configured to indicate a first position of the designated user and to generate a second signal representative of the first position. The surgical system further includes a processor configured to receive the first plurality of signals and the second signal and determine, based on the first plurality of signals, a second position. The processor is also configured to compare the detected sound with a registered voice command of the designated user stored in a memory to verify the designated user's credentials, and to send a command signal to a surgical instrument to carry out an operation related to the voice command based on at least one of the verification of the designated user's credentials, the first position, and the second position.

In one embodiment the detected sound is a voice command generated by the designated user. The voice command is detected by at least one voice sensor in a headset worn by the designated user. In one implementation the headset includes a camera configured to detect a motion of lips of the designated user during the generation of the voice command and to send a signal related to the detection to the processor. In another implementation the processor is configured to determine whether the detected motion of lips of the designated user matches the generated voice commands and to send the command signal when the detected motion of lips of the designated user matches the generated voice commands.

In one embodiment the voice command is detected by at least one voice sensor disposed on the surgical instrument. In another embodiment the second position is determined based on one or more delays in detection of the sound by one or more of the plurality of voice sensors. In yet another embodiment, the processor is configured to send the command signal when the difference between the first position and the second position is less than a predetermined value.

In one embodiment, the processor is configured to compare the detected sound with the registered voice command using a voice recognition algorithm. In another embodiment, the surgical instrument includes a switch and the surgical instrument carries out the operation related to the voice command when the switch is actuated. In yet another embodiment, the processor is configured to send the command signal based on at least two of the verification of the designated user's credentials, the first position, and the second position.

In another aspect, a robotic surgical system includes a robotic arm, a tool assembly removably coupled to the robotic arm and comprising a shaft extending distally from a housing and an end effector coupled to a distal end of the shaft, the end effector being configured to treat tissue. The robotic surgical system also includes a plurality of voice sensors located in a surgical environment housing the robotic arm and configured to detect sound and generate a first plurality of signals. The robotic surgical system further includes a position indicator, in proximity to a designated user, configured to indicate a first position of the designated user and generate a second signal representative of the first position. The robotic surgical system also includes a processor configured to receive the first plurality of signals and the second signal, and determine, based on the first plurality of signals, a second position. The processor is also configured to compare the detected sound with a registered voice command of the designated user stored in a memory to verify the designated user's credentials, and to send a command signal to the tool assembly to carry out an operation related to the voice command based on at least one of the verification of the designated user's credentials, the first position and the second position.

In one embodiment, the second position is determined based on one or more delays in detection of the sound by one or more of the plurality of voice sensors.

In another aspect a method comprises detecting, by a plurality of voice sensors, sound produced in a surgical environment; indicating, by a position sensor, a first position associated with a designated user; determining, based on the detected sound, a second position; comparing the detected sound with registered voice commands stored in a memory to verify the designated user's credentials; and sending a command signal to a surgical instrument to carry out an operation related to the voice command based on at least one of the verification of the user's credential, the first position, and the second position. In one aspect, the, designated user's voice is preregistered for command authenticity and the stored in memory.

In one implementation of the method, the second position is determined based on one or more delays in detection of the sound by one or more of the plurality of voice sensors. In another aspect, the processor sends the command signal when the difference between the first position and the second position is less than a predetermined value. In yet another implementation of the method, the processor sends the command signal based on at least two of the verification of the designated user's credentials, the first position, and the second position.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The systems, devices, and methods disclosed herein can be implemented using a robotic surgical system. WIPO Patent Publication No. WO 2014/151621 filed on Mar. 13, 2014 and entitled "Hyperdexterous Surgical System" is incorporated by reference.

In general, a surgical system is described that allows a user (e.g., a surgeon) in a surgical environment to control the operation of a surgical instrument by voice commands. The surgical instrument can be part of a robotic surgical system. A surgeon performing a surgery (e.g., minimally invasive surgery) may have to perform several surgical tasks, which occur simultaneously and/or which may be actuated by a robotic surgical system. Therefore, it can be desirable for the surgeon to be able control the operation of a surgical instrument by using voice commands.

A surgical system that allows for voice control of surgical instrument must be configured in such a way that the system first ensures that the command is an actionable command that is made by an authorized user (e.g., a surgeon). Thus, the system must authenticate the voice command generated by the user. The authentication protocol can be a single step authentication protocol or a multi-step authentication protocol. In one aspect, the system will register a voice command for a designated user, which can be stored in memory, and used for subsequent authentication of voice commands. The authentication protocol involves one or more of the following: verifying that the voice command is issued by a designated or authorized user (such as by comparison with a registered voice), verifying the authenticity of the voice command based on the location of the source of the voice command, and verifying the authenticity of voice command by capturing the motion of the lips of the designated user and deciphering the corresponding spoken phrase. Optionally, the spoken phrase captured by detecting the motion of the designated user's lips can be compared to the detected voice command.

In one example, the surgical system can use a voice recognition technology to ensure that the voice command is generated by a designated user. Additionally or alternately, the surgical system can determine the authenticity of the voice command based on the location of the source of the voice command. For example, the surgical system can detect the position of the designated user by a position indicator, and compare the detected position with a location of a sound source in the surgical environment measured using multiple voice sensors. Based on the comparison, the surgical system can determine whether the designated user is also the source of sound in the surgical area. The surgical system can also verify the authenticity of a voice command by capturing the motion of the lips of the designated user and deciphering the corresponding spoken phrase. Optionally, the deciphered phrase can be compared with the detected voice command. Following authentication of the voice command based on one or more of the techniques mentioned above, the surgical system will generate a command signal to control the operation of the surgical instrument in a manner consistent with the voice command.

Figure 1:
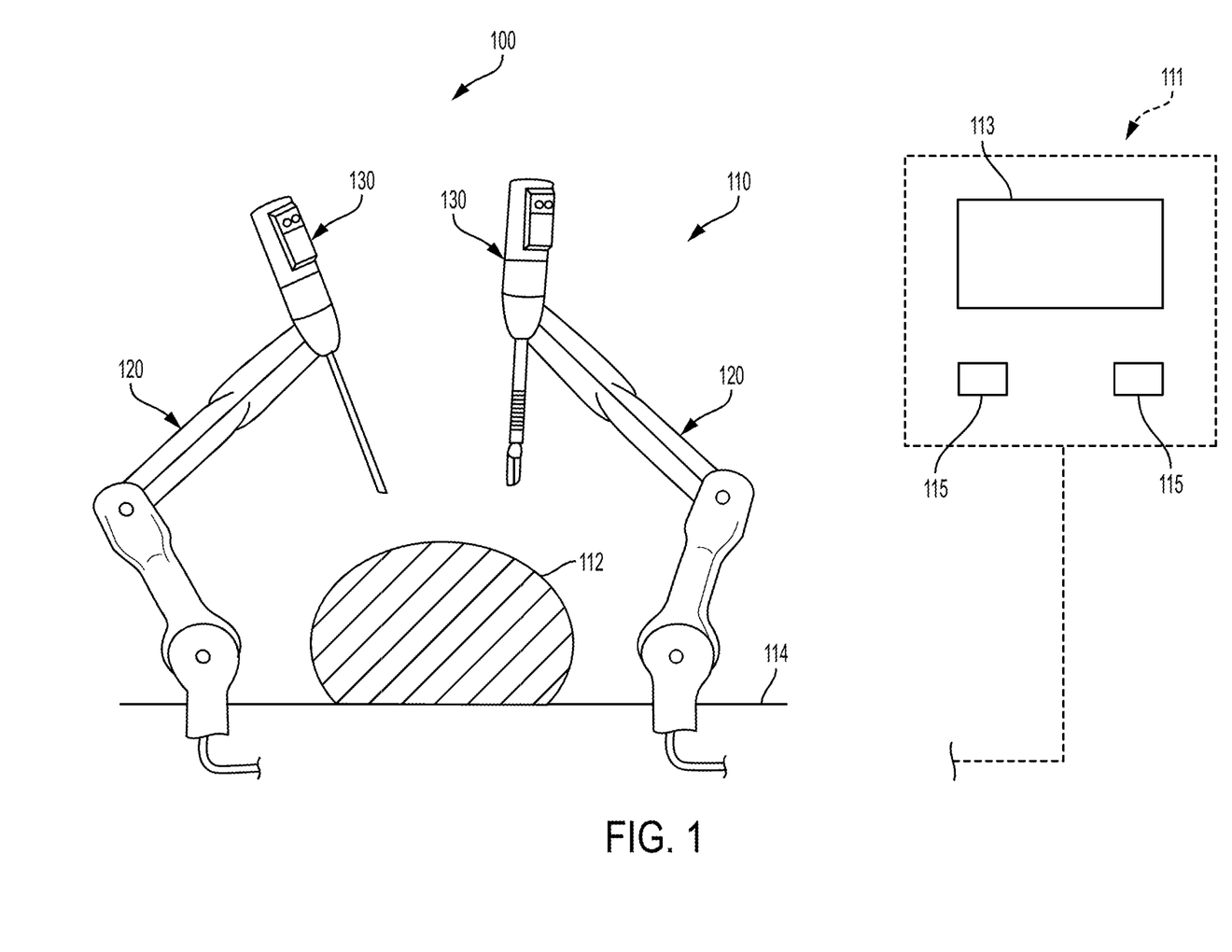
FIG. 1 illustrates a perspective view of an embodiment of a surgical robotic system that includes a patient-side portion and a user-side portion.

FIG. 1 is a perspective view of one embodiment of surgical robotic system 100 that can be used in telesurgery. The system 100 includes a patient-side portion 110 that is positioned adjacent to a patient 112, and a user-side portion 111 that is located a distance from the patient, either in the same room and/or in a remote location. The patient-side portion 110 generally includes one or more robotic arms 120 and one or more tool assemblies 130 that are configured to releasably couple to a robotic arm 120. The user-side portion 111 generally includes a vision system 113 for viewing the patient 112 and/or surgical environment, and a control system 115 for controlling the movement of the robotic arms 120 and each tool assembly 130 during a surgical procedure.

The control system 115 can have a variety of configurations and it can be located adjacent to the patient, e.g., in the operating room, remote from the patient, e.g., in a separate control room, or it can be distributed at two or more locations. As an example of a dedicated system, a dedicated system control console can be located in the operating room, and a separate console can be located at a remote location. The control system 115 can include components that enable a user to view a surgical environment of a patient 112 being operated on by the patient-side portion 110 and/or to control one or more parts of the patient-side portion 110 (e.g., to perform a surgical procedure at the surgical environment). In some embodiments, the control system 115 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 120 and tool assemblies 130.

The patient-side portion can also have a variety of configurations. As depicted in FIG. 1, the patient-side portion 110 can couple to an operating table 114. However, in other embodiments, the patient-side portion 110 can be mounted to a wall, to the ceiling, to the floor, or to other operating room equipment. Further, while the patient-side portion 110 is shown as including two robotic arms 120, more or fewer robotic arms 120 can be included. Furthermore, the patient-side portion 110 can include separate robotic arms 120 mounted in various positions, such as relative to the operating table 114. Alternatively, the patient-side portion 110 can include a single assembly that includes one or more robotic arms 120 extending therefrom.

Figure 2:
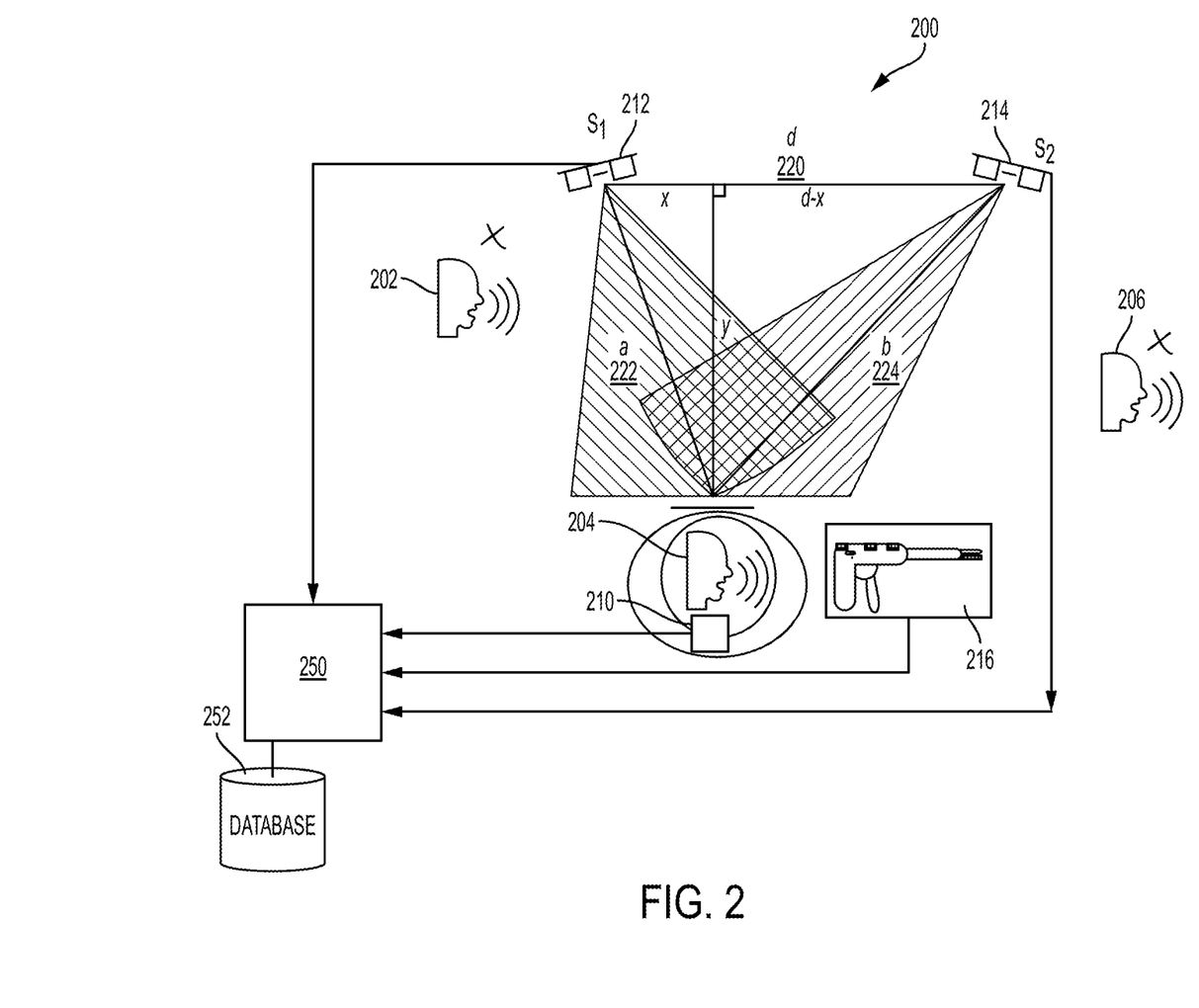
FIG. 2 illustrates a surgical environment comprising a surgical system configured to allow voice control of a surgical instrument.

FIG. 2 is a schematic view of a surgical environment 200 that includes a surgical system configured to allow voice control of a surgical instrument 216. The surgical environment can include several personnel (e.g., surgeons or other medical professionals) 202, 204, 206. A surgeon (e.g., the person designated with reference numeral 204) can be assigned as a designated user to control the operation of the surgical instrument 216. A position indicator 210 is positioned in proximity to designated user 204 and it is configured to detect the position of the designated user 204. For example, the position indicator 210 can be secured to the body of the designated user (e.g., located in a wrist band or a headset worn by the designated user, or placed on the chest of the designated user). The surgical system also includes several voice sensors (e.g., 212, 214, etc.) configured to detect sound produced in the surgical environment 200 (e.g., voice of the personnel 202, 204, 206). The surgical system further includes a processor 250 that is responsible for voice command authentication as well as the control of the operation of the surgical instrument 216. For example, the processor 250 can communicate with the voice sensors 212, 214 positon indicator 210, and surgical instrument 216. Further, processor 250 can save data to and/or retrieve data from a database 252. Signals in the surgical system (e.g., between processor 250 and the position indicator 210, voice sensors 212 and 214, and processor 250, surgical instrument 216 etc.) can be communicated wirelessly (e.g., via Bluetooth, WiFi, etc.) or through a data cable (e.g., optical fiber, coaxial cable, etc.). It is understood that the processor and the surgical system can be part of a robotic surgical system, however the present disclosure is applicable to non-robotic surgical systems as well.

As noted above, the surgical system can allow a user (e.g., designated user 204) to control the surgical instrument 216 once the system successfully completes one or more authentication steps. A user can be assigned as a designated user prior to the start of the surgical procedure. For example, a user can specify to the surgical system that he/she is the designated user by verifying his/her credentials (e.g., by logging into the system using a password, by swiping an identification (ID) card, etc.). The surgical system can ensure that information associated with the designated user that is necessary to allow the designated user to use voice control to actuate the surgical instrument 216 (e.g., the user's voice) is stored in the database 252. Such information can include, for example, voice recordings of the designated user. The designated user 204 (or any other personnel) can also indicate to the surgical system the identity of the surgical instrument 216 to be operated via voice control. In one aspect the designated user 204 can be assigned a positon indicator 210 that allows the system to locate the designated user in the surgical environment. The position indicator 210 can wirelessly (e.g., Bluetooth, WiFi, etc.) communicate with the processor 250, either directly or through another device.

The surgical system can also include voice sensors (e.g., 212, 214, etc.) that can be distributed in the surgical environment 200. For example, the voice sensors can be located on walls in the surgical environment, on the surgical instrument 216, on the operating table, mounted on stands affixed to the floor, etc. The voice sensors can detect a sound generated in the surgical environment and send a signal to the processor 250 indicating the time at which the sound was detected. The processor 250 receives signals indicating the time of detection from the various voice sensors in the surgical environment 200, and the location of the source of sound can be ascertained using a triangulation algorithm. In one embodiment, the triangulation algorithm can be based on the assumption that the time at which a voice sensor detects the sound is proportional to the distance between the source of sound and the voice sensor. Voice sensors that are farther away from the source of sound detect the sound at a later time. For example, sensor 212 (or sensor 214) will detect the sound produced by designated user 204 after a time period that is proportion of the distance "a" 222 (or "b" 224). The processor 250 can determine the difference in time of detection of the various sensors. The processor 250 can use this information, information related to the position of the various voice sensors/separation between the sensors (e.g., separation of "d" 220 between sensors 212 and 214), and the speed of sound in air in the triangulation algorithm (e.g., algorithm that solves an "inverse problem") to determine the position of the source of sound.

If the position of the designated user 204 indicated by the position indicator 210 is within a predetermined distance (e.g., 1 foot, 2 feet, 3 feet, etc., which can be stored in database 252) from the determined location of the source of sound, the processor 250 can conclude that the designated user 204 is also the source of the detected sound. In this case, the processor 250 will generate a command signal for the surgical instrument that is consistent with the voice command issued by the designated user 204. In the event that the sound generated by a person (e.g., 202, 206) who is not the designated user 204 is determined not to be located within the predetermined distance, based on the position measurement from the position indicator 210 and the determined location of the source of sound, the processor 250 will not generate a command signal for the surgical instrument 216.

As noted above, one or more voice sensors can be located in proximity to the designated user to detect sound generated by the user. For example, a microphone can be attached to a headset worn by the designated user, or it can be hung around the designated user's neck. The microphone can be located, for example, a specified distance (e.g., 6-12 inches) from the user's mouth. A variety of microphones can be used, but in one embodiment the microphone has a limited range of sound detection. For example, the microphone may be configured to detect sound generated within a 6-12 inch radius. Such a sound pickup limitation can increase the possibility that the microphone captures the sound generated only by the designated user.

Once the microphone captures designated user's voice, a signal related to the voice is communicated to the processor 250. The processor 250 then compares the designated user's voice with the voice recordings of the designated user stored in the database 252. In one embodiment a voice recognition algorithm can be used to verify a match between the stored sample of the designated user's voice and the voice detected by the voice sensor(s). Additionally, the captured designated user's voice can be stored in the database 252 and can be used to train the surgical system (e.g., using machine learning algorithms) to detect voice command of the designated user with greater accuracy. The processor 250 can also determine whether the designated user's voice matches predetermined voice commands for the surgical instrument 216. For example, the processor 250 can retrieve a voice command data file associated with the surgical instrument 216 from the database 252, and compare them with the designated user's voice. For example, the voice commands for an endocutter can include "move right," "move left," "move up," "move down," "clamp," "unclamp," "release," "cut," "stitch," "seal," "fire," "squeeze," etc. In some embodiments, the designated user may be required to say a password or an initiation word (e.g., "begin") before issuing the voice command for the surgical instrument 216. For example, the designated user may have to say "begin cut" for the processor 250 to generate a command signal that instructs an endocutter in the surgical system to cut a tissue. In such a case the command "cut," by itself, will not be effective to generate a command signal from the processor to the instrument to initiate cutting tissue. In some embodiments, after detecting the voice command from the designated user, the surgical system may repeat the voice command, and ask the designated user for confirmation (e.g., by saying "yes" or "no"). For example, after the designated user has said "begin cut," the surgical system can repeat the voice command and ask the designated user for permission to proceed. If the designated user answers in an affirmative (e.g. "yes," "proceed," etc.) the processor 250 will generate a command signal instructing the endocutter in the surgical system to proceed with cutting the tissue. In some embodiments, the voice commands can include the name of the surgical instrument 216. For example, the designated user may say "Move grasper right" to instruct a grasper to move to the right.

If the processor 250 does not recognize the voice captured by the microphone (e.g., when the microphone captures the voice of the persons 202 or 206), a command signal is not generated. In some embodiments, processor 250 may inform the personnel in the surgical environment 200 that the captured voice could not be recognized (e.g., by an announcement through a speaker in the surgical environment 200). If the processor 250 does not find a match between the voice command by the designated user and the voice commands in the voice command data file associated with the surgical instrument 216, a command signal is not generated. Additionally, the personnel in the surgical environment 200 are notified that a command signal will not be generated.

In some embodiments, certain functions of the surgical instrument can be controlled by a user who may not be the designated user. For example, the surgical system may be configured to allow a trainer and/or supervisory surgeon to control certain predetermined operations of the surgical instrument 216. For example, a trainer can stop or pause the operation of the surgical instrument configured to be used based on voice command of the designated user. The trainer can control the predetermined operations of the surgical instrument 216 by sending a control signal to the processor 250 using an input device. Alternately or additionally, the surgical system can be configured to capture and verify the voice command of the trainer. For example, the trainer can have a microphone and a position indicator which allow the surgical system to capture and verify the voice command of the trainer in a manner similar to that of the designated user described above. The surgical system can be configured to operate in a "training mode" in which one or more trainers can control the predetermined operations of the surgical instrument 216. Once the training mode is turned off, the privileges of the trainers can be rescinded.

The surgical environment 200 can include a filter (e.g., band-pass filter, low-pass filter, high-pass filter) that allows acoustic frequency within a certain range to be captured and/or stored. In one embodiment, the filter can include an acoustic filter coupled with the microphone configured to capture the designated user's voice. Additionally, or alternately, the voice sensors (e.g., 212, 214, etc.) can also include the acoustic filter. The acoustic filter can be a bandpass filter configured to allow acoustic frequencies corresponding to the frequency of designated user's voice. As an example, the bandwidth and location of the band-pass filter can be related to the gender of the designated user (e.g., 85 Hz-180 Hz for an adult male, and 165 Hz-255 Hz for an adult female). In another embodiment, the signal (e.g., voltage or current signal) generated by the microphone can be filtered by an electronic filter (e.g., analog or digital circuit filters). The electronic filters can be programmable (e.g., the bandwidth, filter-type, etc. can be varied). The processor 250 can be configured (e.g., based on a request of a user) to vary the properties of the electronic filter. The electronic filters can be configured to block all frequencies except for a desired band of acoustic frequencies.

Figure 3:
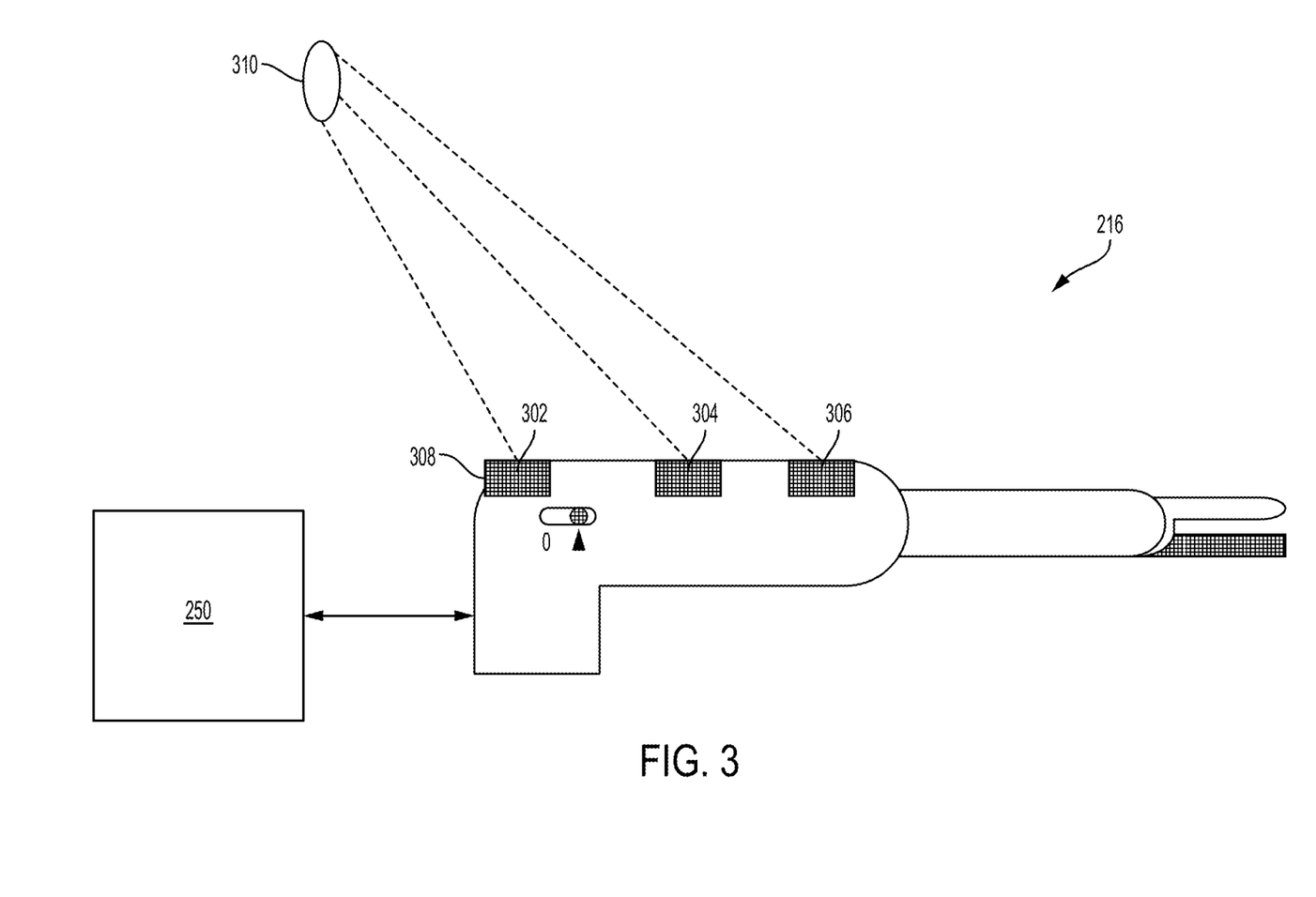
FIG. 3 illustrates an example of the surgical instrument.

FIG. 3 illustrates an example of the surgical instrument 216 (e.g., an endocutter). The surgical instrument 216 can include multiple voice sensors 302, 304, 306 configured to detect sound generated by a source 310 in the surgical environment 200. The surgical instrument 216 can send one or more signals to the processor 250 that include information related to the detected sound, time of detection of sound by the various voice sensors, etc. For example, the voice sensors can detect voice commands generated by the designated user 204. The surgical instrument 216 is also configured to receive command signals from the processor 250 and based on such command signals the instrument can carry out an operation. The surgical instrument 216 can optionally include a switch 318 and in some embodiments the switch is be activated for the surgical instrument 216 to carry out an operation. In some embodiments, the switch 318 can be remoted actuated (e.g., wirelessly through WiFi, Bluetooth, etc.).

Figure 4:
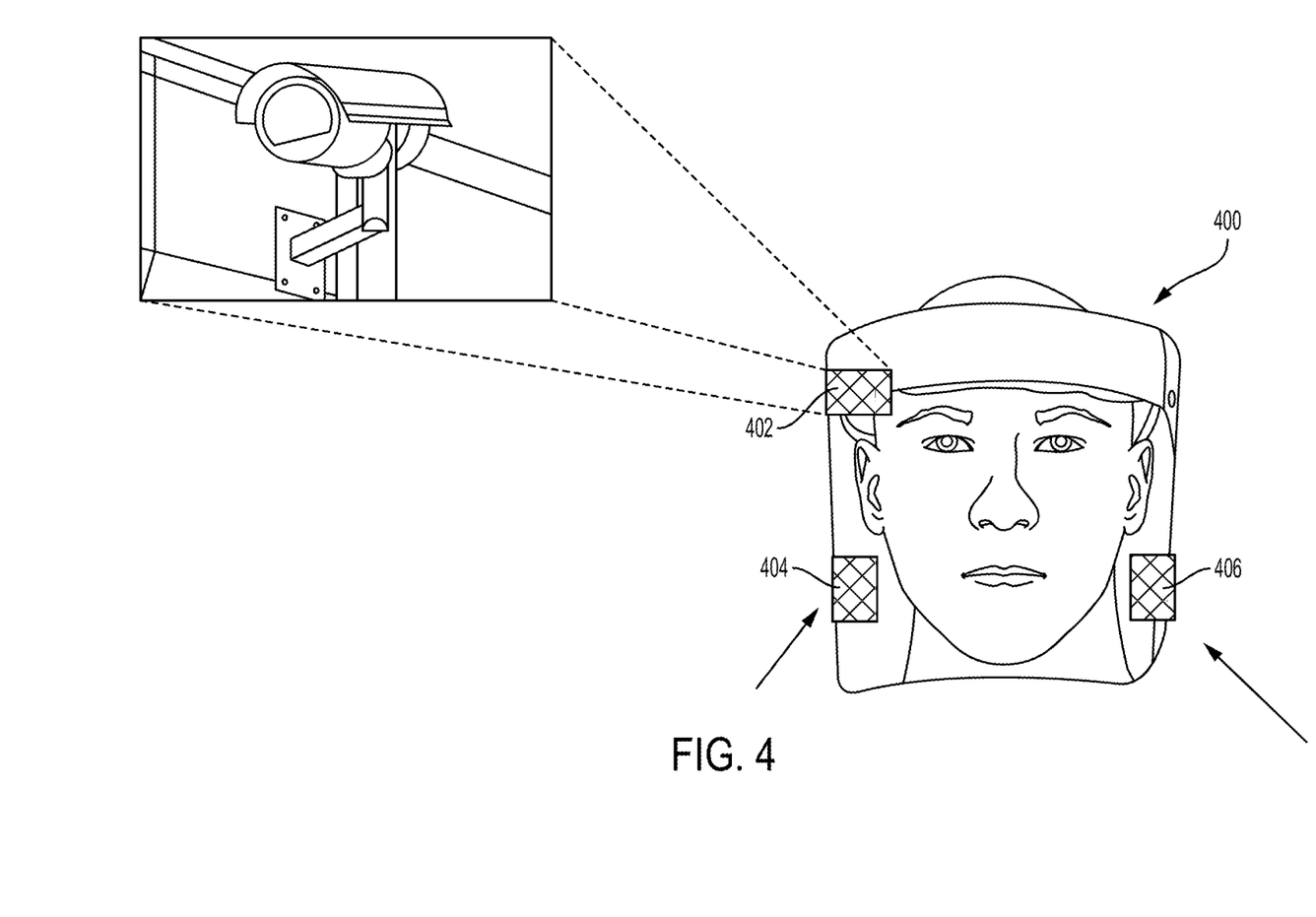
FIG. 4 illustrates an example of a head set worn by a user of the surgical system.

FIG. 4 illustrates an example of a headset 400 that can be worn by the designated user 204. The headset 400 can also include a camera 402 and multiple microphones 404, 406. The microphones are configured to detect a voice signal generated by the designated user 204. The camera 402, which is optional, is configured to capture images of the mouth of the designated user 402. The microphones and the camera 402 are configured to be in communication with the processor 250 (e.g., wirelessly) and to convey information related to captured image and/or detected voice signal to the processor 250. Additionally, information related to the time of detection of the voice signal and image can be conveyed to the processor 250 as well. In one embodiment, the camera is configured to capture the motion of the lips of the designated user during the generation of the voice signal. The processor can use an image recognition algorithm to decipher the words/phrase corresponding to the captured motion of the lips of the designated user. The processor 250 can compare the deciphered words/phrases with the voice signal generated by the designated user approximately at the same time that the corresponding motion of lips is captured. If the result of the attempted authentication is an affirmative (i.e., the deciphered phrase and the voice signal match), the processor 250 will generate a command signal corresponding to the voice signal.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to a user and a keyboard and a pointing device, e.g., a mouse, a trackball, etc., by which a user may provide input to the computer. Other kinds of devices can be used to provide for interaction with a user as well. For example, feedback provided to a user can be any form of sensory feedback, such as for example visual feedback, auditory feedback, or tactile feedback; and input from a user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 5:
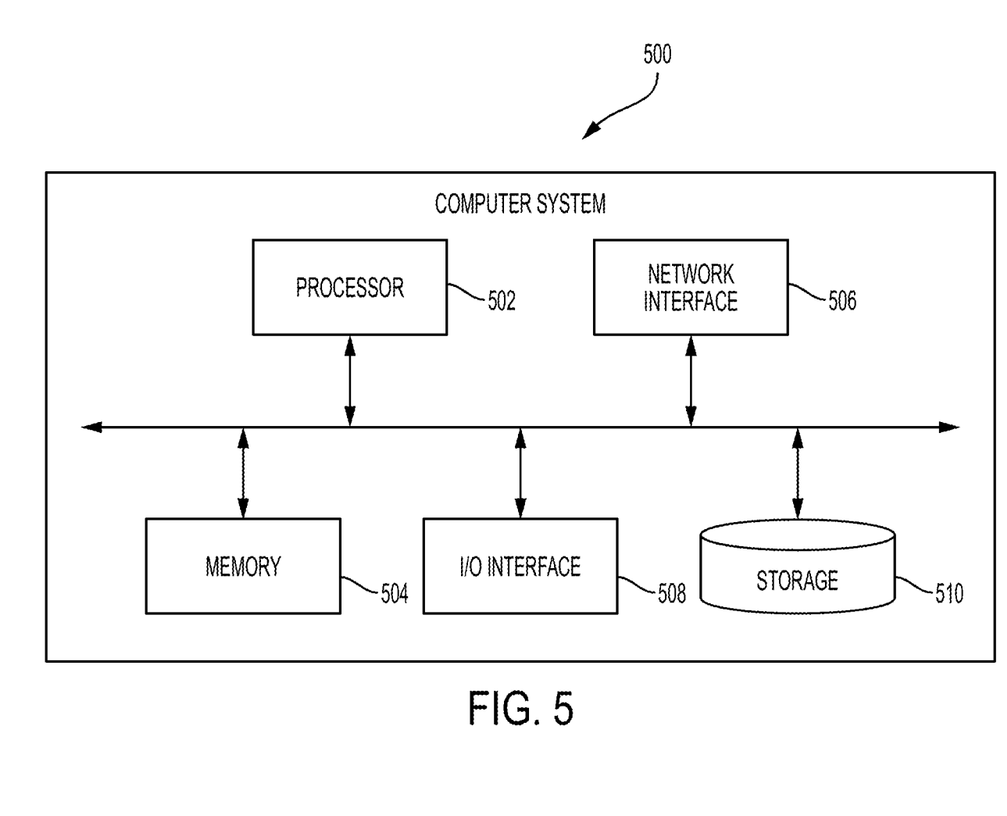
FIG. 5 is a schematic illustration of a computer system configured to generate a plurality of command signals for use with the control system described herein.

FIG. 5 illustrates an exemplary embodiment of a computer system 500. As shown, the computer system 500 includes one or more processors 502 which can control the operation of the computer system 500. "Processors" are also referred to herein as "controllers." The processor(s) 502 can include any type of microprocessor or central processing unit (CPU), including programmable general-purpose or special-purpose microprocessors and/or any one of a variety of proprietary or commercially available single or multi-processor systems. The computer system 500 can also include one or more memories 504, which can provide temporary storage for code to be executed by the processor(s) 502 or for data acquired from one or more users, storage devices, and/or databases. The memory 504 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 500 can be coupled to a bus system 512. The illustrated bus system 512 is an abstraction that represents any one or more separate physical busses, communication lines/interfaces, and/or multi-drop or point-to-point connections, connected by appropriate bridges, adapters, and/or controllers. The computer system 500 can also include one or more network interface(s) 506, one or more input/output (10) interface(s) 508, and one or more storage device(s) 510.

The network interface(s) 506 can enable the computer system 500 to communicate with remote devices, e.g., other computer systems, over a network, and can be, for non-limiting example, remote desktop connection interfaces, Ethernet adapters, and/or other local area network (LAN) adapters. The IO interface(s) 508 can include one or more interface components to connect the computer system 500 with other electronic equipment. For non-limiting example, the IO interface(s) 508 can include high speed data ports, such as universal serial bus (USB) ports, 1394 ports, Wi-Fi, Bluetooth, etc. Additionally, the computer system 500 can be accessible to a human user, and thus the IO interface(s) 508 can include displays, speakers, keyboards, pointing devices, and/or various other video, audio, or alphanumeric interfaces. The storage device(s) 510 can include any conventional medium for storing data in a non-volatile and/or non-transient manner. The storage device(s) 510 can thus hold data and/or instructions in a persistent state, i.e., the value(s) are retained despite interruption of power to the computer system 500. The storage device(s) 510 can include one or more hard disk drives, flash drives, USB drives, optical drives, various media cards, diskettes, compact discs, and/or any combination thereof and can be directly connected to the computer system 500 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 5 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 500 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 500 can also include a web server for generating and/or delivering the web pages to client computer systems.

In an exemplary embodiment, the computer system 500 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   a plurality of voice sensors located in a surgical environment and configured to detect sound and generate a first plurality of signals;
   a position indicator, in proximity to a designated user, configured to indicate a first position of the designated user and generate a second signal representative of the first position; and
   a processor configured to:
      receive the first plurality of signals generated by the voice sensors and the second signal,
      determine, based on the first plurality of signals, a second position, compare the detected sound with a registered voice command of the designated user stored in a memory to verify the designated user's credentials, and send a command signal to a surgical instrument to carry out an operation related to the voice command based on at least one of the verification of the designated user's credentials, the first position, and the second position.

2. The system of claim 1, wherein the detected sound is a voice command generated by the designated user.

3. The system of claim 2, wherein the voice command is detected by at least one voice sensor in a headset worn by the designated user.

4. The system of claim 3, wherein the headset includes a camera configured to detect a motion of lips of the designated user during the generation of the voice command and to send a signal related to the detected motion of lips to the processor.

5. The system of claim 4, wherein the processor is configured to determine whether the detected motion of lips of the designated user matches the generated voice commands and to send the command signal when the detected motion of lips of the designated user matches the generated voice commands.

6. The system of claim 2, wherein the voice command is detected by at least one voice sensor disposed on the surgical instrument.

7. The system of claim 1, wherein the second position is determined based on one or more delays in detection of the sound by one or more of the plurality of voice sensors.

8. The system of claim 1, wherein the processor is configured to send the command signal when the difference between the first position and the second position is less than a predetermined value.

9. The system of claim 1, wherein the processor is configured to compare the detected sound with the registered voice command using a voice recognition algorithm.

10. The system of claim 1, wherein the surgical instrument includes a switch and the surgical instrument carries out the operation related to the voice command when the switch is actuated.

11. The system of claim 1, wherein the processor is configured to send the command signal based on at least two of the verification of the designated user's credentials, the first position, and the second position.

12. A robotic surgical system, comprising:
a robotic arm;
a tool assembly removably coupled to the robotic arm and comprising a shaft extending distally from a housing and an end effector coupled to a distal end of the shaft, the end effector being configured to treat tissue;
a plurality of voice sensors located in a surgical environment housing the robotic arm and configured to detect sound and generate a first plurality of signals;
a position indicator, in proximity to a designated user, configured to indicate a first position of the designated user and generate a second signal representative of the first position; and
a processor configured to:
receive the first plurality of signals generated by the voice sensors and the second signal,
determine, based on the first plurality of signals, a second position,
compare the detected sound with a registered voice command of the designated user stored in a memory to verify the designated user's credentials, and
send a command signal to the tool assembly to carry out an operation related to the voice command based on at least one of the verification of the designated user's credentials, the first position, and the second position.

13. The robotic surgical system of claim 12, wherein the second position is determined based on one or more delays in detection of the sound by one or more of the plurality of voice sensors.

14. A method of controlling a surgical instrument, comprising:
detecting, by a plurality of voice sensors, sound produced in a surgical environment;
generating, by the voice sensors, a first plurality of signals;
indicating, by a position sensor, a first position associated with a designated user;
determining, based on the first plurality of signals, a second position;
comparing the detected sound with registered voice commands stored in a memory to verify the designated user's credentials; and
enabling a surgical instrument to carry out an operation related to the voice command based on at least one of the verification of the user's credential, the first position, and the second position.

15. The method of claim 14, further comprising registering the designated user's voice.

16. The method of claim 15, wherein the registered voice is stored in memory.

17. The method of claim 14, wherein the second position is determined based on one or more delays in detection of the sound by one or more of the plurality of voice sensors.

18. The method of claim 14, wherein the processor sends the command signal when the difference between the first position and the second position is less than a predetermined value.

19. The method of claim 14, wherein the processor sends the command signal based on at least two of the verification of the designated user's credentials, the first position, and the second position.

* * * * *